United States Patent
Scholz et al.

(10) Patent No.: US 8,753,286 B2
(45) Date of Patent: Jun. 17, 2014

(54) SPIROMETER WITH REPLACEABLE FLOW TUBE

(75) Inventors: Alexander Scholz, Bischofswiesen (DE); Murat Gül, München (DE)

(73) Assignee: sendsor GmbH, Munich (DE)

( * ) Notice: Subject to any disclaimer, the term of this patent is extended or adjusted under 35 U.S.C. 154(b) by 674 days.

(21) Appl. No.: 12/978,388

(22) Filed: Dec. 23, 2010

(65) Prior Publication Data
US 2011/0125045 A1  May 26, 2011

Related U.S. Application Data

(63) Continuation of application No. PCT/EP2009/004517, filed on Jun. 23, 2009.

(30) Foreign Application Priority Data

Jun. 27, 2008 (DE) .................. 10 2008 030 536

(51) Int. Cl.
*A61B 5/085* (2006.01)
*A61B 5/09* (2006.01)
*A61B 5/097* (2006.01)

(52) U.S. Cl.
USPC ........... 600/538; 600/529; 600/532; 600/533; 600/537; 600/539; 600/540; 600/543

(58) Field of Classification Search
CPC ........ A61B 5/087; A61B 5/091; A61B 5/097; A61M 2016/003
USPC ................. 600/529–543; 128/200.24–207.29
See application file for complete search history.

(56) References Cited

U.S. PATENT DOCUMENTS

| | | | |
|---|---|---|---|
| 3,735,752 A * | 5/1973 | Rodder | 600/537 |
| 4,905,709 A | 3/1990 | Bieganski et al. | |
| 5,277,196 A | 1/1994 | Hankinson et al. | |
| 5,363,842 A | 11/1994 | Mishelevich et al. | |
| 5,518,002 A * | 5/1996 | Wolf et al. | 600/538 |
| 5,564,432 A | 10/1996 | Thomson | |
| 5,676,132 A * | 10/1997 | Tillotson et al. | 128/204.23 |
| 5,715,831 A | 2/1998 | Johnson | |
| 6,073,480 A * | 6/2000 | Gokhfeld | 73/29.02 |
| 6,126,613 A * | 10/2000 | Edwards et al. | 600/539 |
| 6,899,683 B2 * | 5/2005 | Mault et al. | 600/531 |
| 6,955,650 B2 * | 10/2005 | Mault et al. | 600/531 |
| 2002/0138213 A1 * | 9/2002 | Mault | 702/32 |
| 2003/0116159 A1 * | 6/2003 | Orr et al. | 128/204.23 |
| 2003/0216659 A1 * | 11/2003 | Brawner et al. | 600/532 |
| 2004/0039295 A1 * | 2/2004 | Olbrich et al. | 600/538 |
| 2008/0200824 A1 * | 8/2008 | Kane et al. | 600/532 |

FOREIGN PATENT DOCUMENTS

| | | |
|---|---|---|
| DE | 102006024363 | 11/2007 |
| GB | 2388665 | 11/2003 |
| WO | 9720500 | 6/1997 |
| WO | 0156454 | 8/2001 |
| WO | 02071017 | 9/2002 |
| WO | 03024317 | 3/2003 |

* cited by examiner

*Primary Examiner* — Jacqueline Cheng
*Assistant Examiner* — Puya Agahi
(74) *Attorney, Agent, or Firm* — Smartpat PLC; Axel Nix

(57) ABSTRACT

The invention relates to a spirometer for measuring pulmonary respiration of a test subject, comprising a body and a sensor unit, wherein the sensor unit can be interchanged with further sensor units. In a corresponding method, such a spirometer is operated with a sensor unit and the sensor unit is subsequently interchangeably replaced by a further sensor unit.

15 Claims, 2 Drawing Sheets

SPIROMETER WITH REPLACEABLE FLOW TUBE

TECHNICAL FIELD

The present disclosure relates to a spirometer for measuring pulmonary respiration of a test subject by means of a mass flow sensor, a humidity sensor, a temperature sensor, and a pressure sensor.

BACKGROUND

Devices for measuring lung functions include, for example, spirometers or pneumotachographs, by means of which lung volume or a respiratory characteristic of a test subject can be determined over a period of time. A time curve of the breathing pressure and breathing volume is of particular interest for diagnosing existing or incipient respiratory illnesses or other pathologies in the context of the respiratory system of a test subject. Determining a volume flow over time of the air inhaled or exhaled by a test subject is particularly desirable.

Directly determining the volume flow of respiration in the conventional manner, however, is difficult, and requires corresponding sensors that are typically prone to failure or contamination. For example, a sensor having a turbine wheel that can directly measure a volume flow can be used for measuring volume flow in a spirometer. Such sensors, however, are generally relatively expensive, and must also be located directly in the flow of the breathing air of a patient. They are thereby unavoidably exposed to contamination by saliva or potentially by pathogens, so that extensive cleaning measures and regular functional checks are necessary.

Conventional windmill-type spirometers and pneumotachographs based on volume flow sensors also require extensive calibration to guarantee the accuracy of measurements.

SUMMARY

The present disclosure provides a spirometer for measuring pulmonary respiration of a test subject that is less difficult to use and maintain, and that is less prone to contamination than known spirometers. The disclosed spirometer is both hygienic and inexpensive. Further disclosed is a method for operating the improved spirometer.

A device according to the present teachings serves for measuring pulmonary respiration of a test subject, particularly determining a volume flow during respiration, and can therefore also be designated a spirometer. A test subject is particularly a human patient. The spirometer comprises a body and a sensor unit. The sensor unit comprises a tubular member through which air can flow. This tubular member is referred to as a flow tube. A test subject can blow air out or draw air in through the flow tube, i.e. the test subject can inhale or exhale through the flow tube. In doing so, the entire volume of air inhaled or exhaled by the test subject passes through the flow tube. The flow tube can extend into or be attached to a mouthpiece, making it easier to apply the test subject's mouth while avoiding air leakage when blowing into the flow tube.

The sensor unit comprises a mass flow sensor, which is configured to measure a mass flow of air passing through the flow tube. The mass flow sensor is preferably disposed within the flow tube. The mass flow sensor produces an electrical signal output which changes in response to the amount of air mass passing through the flow tube. By processing the output of the mass flow sensor the entire mass of air passing through the flow tube and the mass flow over the course of time can be determined. When a test subject blows into the flow tube of the sensor unit, the entire mass of air passing through the flow tube can be measured by processing the output of the mass flow sensor. Also, the mass flow, which is a time derivative of the total mass of flowing air, can be measured by processing the output of the mass flow sensor. In contrast to a volume flow sensor, a mass flow sensor does not need to be calibrated for potentially variable external parameters, such as air pressure, humidity, or temperature, because the mass flow can be measured independently of these external parameters.

The mass flow sensor may comprise a first temperature element, such as a 6.8 Ohm platinum resistive thermal device (Pt 6.8 RTD). This exemplary temperature element comprises a wire, which is heated to a predetermined temperature, and maintained at this target temperature. Air passing through the flow tube flows across the wire cools the wire off as the air passes. Additional heating power is applied to the wire, in order to compensate the cooling and maintain a constant temperature of the wire. The amount of heating power needed to maintain a constant target temperature of the wire can be used to determine a mass flow over time of the air passing through the flow tube. The electrical signal output of the mass flow sensor equals the amount of power required to maintain the target temperature of the wire.

The cooling of the wire depends on the temperature of the wire relative to the temperature of air passing through the flow tube. Hence, it is advantageous to measure the temperature of air passing through the flow tube. This can be done by a second temperature element, e.g. a 1000 Ohm platinum RTD element. The wire of the first temperature element is heated to a predetermined delta temperature above the temperature of the air passing through the flow tube. A measuring bridge consisting of the first temperature element and the second temperature element may be used.

In a specific example the temperature of the air passing through the flow tube may be 37° C. This temperature of 37° C. is measured by the second temperature element. A predetermined temperature delta of, for example, 200° C., is added to the measured temperature of 37° C. to determine the target temperature of the first temperature element. The first temperature element is hence maintained at a resulting target value of 237° C.

The sensor unit can be removably attached to the body of the spirometer, whereby a data connection is established between the sensor unit and the body. A data exchange between the sensor unit, particularly the mass flow sensor thereof, and the body, is possible by means of the data connection. The data connection can be based on electrical conductivity, such as by means of a cable, but can also function wirelessly, such as by electromagnetic induction, radio, or infrared communication. Both the sensor unit and the body comprise communication means, such as electrical conductors and contacts, induction couplings, or radio transmitters and receivers or infrared transmitters and receivers. A plurality of types of communication can be provided in parallel. A plurality of corresponding communication means are then provided for the sensor unit and body. The communication between the sensor unit and the body may be bidirectional. Sensor values representing the mass flow sensor within the sensor unit are communicated to the body. Data may also be communicated from the body to the sensor unit, or the sensor within the sensor unit.

The ability to removably attach the sensor unit to the body can be based on a releasable mechanical contact. The sensor unit can, for example, be fit, slid, or glued on to the body, or hooked or inserted into the body. It is also possible that a build-up of an electrical contact, such as by means of electrically conductive plug connections, also allows a releasable attachment between the sensor unit and the body, so that additional, purely mechanical contacts are not needed.

The body of the spirometer comprises one or more ambient air sensors adapted to sense an ambient air characteristic, e.g. temperature sensor, a humidity sensor, or a pressure sensor. Using the humidity sensor of the body, the ambient air humidity level at the body can be measured, and used to approximate the air humidity level at the sensor unit. If the sensor unit is attached to the body, a corresponding spatial proximity of said two units exists, so that the ambient air humidity measured at the humidity sensor of the body approximates the air humidity at the sensor unit. Ambient air pressure at the body, and thus approximately air pressure at the sensor unit, can also be correspondingly measured by means of the pressure sensor of the body. Deviations of air humidity or air pressure around the spirometer are extremely small, and, as a rule, are negligible for measurements using corresponding sensors. Accordingly, a ambient air temperature at the body can also be measured using the temperature sensor of the body, substantially corresponding to the temperature in the environment of the entire spirometer.

A mass flow sensor is provided in the sensor unit, the functional principle of which was described in the example above. The construction thereof, even with one or more heating elements, is substantially simpler than the construction of a volume flow sensor, which is based, for example, on a turbine wheel having moving parts. While a volume flow sensor is exposed to a large degree to contamination by saliva from the mouth of the test subject, and thus provides space for the growth or transmission of pathogens, a sensor unit having a mass flow sensor is substantially less exposed to contaminants and is thus significantly more hygienic. A mass flow sensor is also typically considerably less expensive to produce and operate than a volume flow sensor. The spirometer thus provides increased hygiene in application, as well as a reduction in cost relative to a solution using a volume flow sensor, wherein the quality of the measurement results is, however, comparable.

In one aspect of the disclosure a single body is used with replaceable sensor units. Since the sensor unit is removably attached to the body, and a data exchange between said two units can be established and removed, one sensor unit can be replaced by other sensor units. For measuring a pulmonary respiration of a test subject, particularly a volume flow of respiration using the spirometer, various sensor units can thereby be sequentially attached to the body, so that data exchange is possible between the sensors of each sensor unit and the sensors of the body.

It is possible to provide multiple identical sensor units for operating with an associated body. Each sensor unit can be disposed of after use, whereas the body can further serve for receiving sensor units, and thus the spirometer can also further serve for measuring pulmonary respiration of a test subject. This means, that a sensor unit can be replaced by an identical sensor unit at any time. Disposable, single-use sensor units are economical by using a relatively inexpensive mass flow sensor in the sensor unit, and locating more expensive components for controlling and evaluating the mass flow sensor in the reusable body. Disposable sensor units would not be economical in combination with more expensive volume flow sensor in the sensor unit.

In this manner, the application of the spirometer is significantly more hygienic relative to conventional spirometers for determining pulmonary respiration of a test subject. The use of a mass flow sensor in place of a volume flow sensor in the sensor unit of the spirometer, as described above, is already substantially more hygienic due to the simple construction of the mass flow sensor. The ability to replace the sensor unit with a further sensor unit thereby significantly increases the hygiene level once again. A test subject can, for example, use the spirometer with a first sensor unit a few times. After the first sensor unit has been replaced with a second, unused, sensor unit, a second test subject can then use the spirometer. In contrast to a conventional spirometer, wherein in the best case a mouthpiece can be replaced, a test subject cannot be exposed to bodily fluids or pathogens from a previous test subject with a spirometer having an interchangeable sensor unit, if an unused sensor unit is used. There is no risk of inhaling particles that are potentially hazardous to the health, particularly when the test subject inhales through the flow tube.

A further sensor unit can, for example, also be used as a spirometer in place of a previous sensor unit, together with the body, if the previous sensor unit is potentially contaminated by pathogens or if the function thereof is affected by contamination. The sensor unit can also be replaced if a further test subject is to have measurements performed and the unit has become unhygienic, and thus unusable, after use. Replacement of the sensor unit is also provided if a measurement using this sensor unit is no longer reproducible or no longer accurate, for example if the sensor unit is defective. The sensor units for the spirometer can be disposable items that are packed individually for sale, and are intended to be disposed of after one or more uses. Because only a single mass flow sensor or single temperature sensor is provided in the sensor unit, the sensor unit can be correspondingly inexpensive and therefore can be produced as a disposable item. Due to the positioning of the relatively expensive sensors for humidity and air pressure in the body, and the provision of only one inexpensive mass flow sensor, and optionally one or two inexpensive temperature sensors, in a sensor unit, the costs for a sensor unit are greatly reduced. The sensor unit further comprises no analysis unit for data, and no further electronics, so that a strict cost limit is possible. The service life of the entire spirometer is simultaneously greatly increased relative to conventional spirometers, by always using new sensor units.

According to a further embodiment, the sensor unit and all further sensor units provided for the spirometer are standardized with respect to a set measurement standard. This is often referred to as calibrating or calibration, and ensures that all measurements performed using the corresponding sensor units will have essentially the same results. Conventional spirometers or pneumotachographs must always be calibrated, and calibration must be repeated at regular intervals or as necessary, so that the corresponding measurement results remain indicative and can be used for diagnosis. Such a calibration can be an elaborate procedure, and can generally be performed only by trained personnel, using special spirometers. For this reason, spirometers must often be sent back to the manufacturer, or to specially trained and equipped personnel, in order to be calibrated there. This causes an appreciable loss of time and corresponding financial expenditure. This is due to the fact that spirometers having volume flow sensors must be continuously calibrated, in order to correct for changes in external parameters that can affect volume flow, such as air pressure, air humidity, or temperature. In order to obtain an accurate measured value using conventional spirometers, a calibration to the current environmental conditions or external parameters must be performed prior to each measurement. A spirometer by means of which such a calibration can be performed, however, is very large and thus not usable for mobile applications. Such spirometers for calibration are also generally too expensive for private users.

This cost and time-intensive calibration is not necessary, however, for a spirometer according to this embodiment, because a plurality of interchangeable sensor units are provided to a user in a calibrated state, or, more accurately, without calibration, and in an unused state, and the corresponding calibration is substantially not affected. This means that a user has attached a sensor unit to the body, while storing further sensor units that are ready to use, in order to use them when needed. A first sensor unit can thus be attached to the body, for example, in order to perform measurements of the pulmonary respiration of a test subject. If the sensor unit is no longer in a calibrated state due to frequent use or due to contamination, then the sensor unit can simply be removed from the body and a further sensor unit, new and unused and therefore calibrated, can be attached to the body. A calibrated sensor unit and calibrated spirometer is then once again available. This process of replacing the sensor unit can, of course, be done very quickly and can be performed even by an untrained assistant or a test subject himself.

The spirometer thus provides the opportunity for hygienic use by one or more users, due to the interchangeability of the sensor unit. In addition, each new sensor unit that is attached to the body provides a newly calibrated spirometer, so that highly accurate measurement results can be obtained without having to calibrate the entire spirometer.

According to a further embodiment, the sensor unit and the further sensor units are standardized with respect to a lung volume of a test subject, or to a set mass flow. This means, that calibration is possible using not only generally standard values, such as the dimensions of the sensor unit or the characteristics of the sensors of the spirometer, but also individually for typical organic parameters of each test subject. A first sensor unit can thus be used for a measurement for a first test subject, for example, that is calibrated to the lung volume or a set mass flow of the first test subject, and then a second sensor unit can be attached to the body after the first sensor unit is removed, in order to take a second measurement for a second test subject, wherein the second sensor unit is individually calibrated for the second patient.

An individual calibration can here not necessarily affect external parameters, but can consider, for example, an expected lung volume or a maximum expected pressure of exhalation. Thus, for example, a first sensor unit can be calibrated for an adult test subject having a large lung volume of 4 liter, and a breathing pressure of 150 mbar, while a second sensor unit is calibrated for a child having a small lung volume of 2 liter and a lower breathing pressure of 40 mbar.

According to one embodiment, the body comprises an analysis unit to which the mass flow sensor of the sensor unit can transfer the measurement data it captured. The analysis unit can determine a corresponding mass flow or a volume flow of the inhalation or exhalation, or a corresponding time trace, or further characteristics of the pulmonary respiration of a test subject, based on the received measured values. An analysis of the measured values can be, for example, a determination of a volume flow of a pulmonary respiration of a test subject.

The analysis unit is provided for capturing, analyzing, or transmitting to further units the measurement data measured by the humidity sensor, the temperature sensor, the pressure sensor, or the mass flow sensor. All of these measurement data can, of course, be captured, analyzed, or transmitted individually or collectively. The analysis unit can send the analyzed data to further spirometers, such as by radio-based, optical, acoustic, electronic, or electrical data transfer.

By analyzing the measurement data from the sensors of the spirometer it is possible to determine a volume flow, without requiring a direct measurement of the volume flow. For this purpose, a progression of the volume flow over time can particularly be determined from the measurement data of the temperature sensor, the pressure sensor, the humidity sensor, and the mass flow sensor. The measurement values measured by said sensors, that is the mass flow values for the air flowing through the flow tube and the measurement values of the air temperature, humidity, and air pressure in the environment of the spirometer can be analyzed together by the analysis unit, in order to determine a corresponding volume flow. A volume flow of the air in the flow tube is thus not directly measured; rather, it is determined indirectly from the measurement values of the sensors of the spirometer.

However, by no means is a volume flow sensor merely replaced with a plurality of sensors for indirectly measuring a volume flow. Rather, different types of sensors are provided also at different positions in the spirometer, allowing a spatial separation of the sensors for determining volume flow, assuming a substantial similarity between the external parameters, such as air pressure in the environment, humidity, and ambient temperature, with the parameters in the immediate environment of a mass flow sensor, which has many advantages. The mass flow sensor to be exposed to breathing air is disposed in the flow tube, while the relatively durable but also expensive sensors for determining the air humidity, the air pressure, and the temperature are disposed in the body. This not only allows calibration-free operation of the spirometer, but the flow tube and mass flow sensor can also be replaced, so that a maximum level of hygiene is possible while minimizing cost and operational effort.

The relationship of mass flow $\dot{m}$ of air flowing through the flow tube, which is measured by the mass flow sensor, and volume flow $\dot{V}$ is established by $$\dot{m} = \dot{V} \cdot \rho \tag{1}$$

with $\rho$ being the air density. Since $\dot{m}$ is the time derivative of the mass m flowing through the flow tube and $\dot{V}$ is the time derivative of the volume of air flowing through the flow tube, it is m=∫$\dot{m}$ dt and V=∫$\dot{V}$dt. Air density $\rho$ is $$\rho = \frac{1}{(T/°C.+273.16)}\left(\frac{p-\varphi \cdot p_S(T)}{R_L} + \frac{\varphi \cdot p_S(T)}{R_D}\right). \tag{2}$$

The mass flow in is thus the product of the volume flow $\dot{V}$ and the pressure r. The relationship for the density $\rho$ includes a conversion of the temperature from degrees Celsius to Kelvin, and the specific gas constant $R_L$ for dry air of $R_L$=287.05 J/kgK and $R_D$ for water vapor of $R_D$=461 J/kgK, for the moist air in the flow tube.

The air humidity j in the breathing air flowing through the flow tube is considered to be a maximum during exhalation, so that this air has the humidity of water vapor. Water vapor itself has a saturation pressure $p_s$, which depends on the temperature of the breathing air, whereby the water vapor pressure $p_D$ results from the following relationship, together with the humidity of the breathing air j from the humidity sensor:

$$p_D = j \cdot p_S \tag{3}$$

The composition for the density $\rho$ results from the sum of the density of dry air $\rho_L$ and the density of water vapor $\rho_D$, and thus $$\rho = \rho_L + \rho_D. \tag{4}$$

Together with the gas constant for dry air $R_L$ of 287.05 J/kgK and the gas constant for water vapor $R_D$ 461 J/kgK, the gas constant of the moist air in the flow tube is as follows:

$$R_F = R_L/(1-(\phi \cdot p_s/p)\cdot(1-R_L/R_D)). \qquad (5)$$

The so-called Magnus formula for the saturation water vapor pressure $p_s$, from DIN 4108, accurate to 0.1%, yields the relationship $$p_s(T) = p_0 \cdot \exp((17.62 \cdot T)/(243{,}12°\,C. + T)), \qquad (6)$$

where $p_0 = 611.2$ Pa and T=temperature in ° C. of the air flowing through the flow tube.

Finally, the volume flow $\dot{V}$ can be determined from the above equations (1) through (6).

$$\dot{V} = \frac{\dot{m} \cdot (T/°\,C. + 273{,}16) K * R_L}{p \cdot \left(1 - \left(\varphi \cdot \frac{p_0 \cdot \exp\left(\frac{17{,}62 * T}{243{,}12°\,C. + T}\right)}{p}\right) \cdot \left(1 - \frac{R_L}{R_D}\right)\right)} \qquad (7)$$

In this manner, the volume flow $\dot{V}$ of the air flowing through the flow tube of the sensor unit can be indirectly determined, so that sensors for directly measuring a volume flow that are prone to failure and difficult to operate can be eliminated. The sensor unit of the spirometer has a mass flow sensor that is both less prone to failure or contamination and less expensive, while sufficiently accurate values for a volume flow can nevertheless be determined.

This determination of the volume flow $\dot{V}$ from the measurement values of the sensors of the spirometer and from the specified assumptions about physical environmental parameters in the flow tube can be implemented in a method, in which the measurement values listed above are obtained from the sensors and processed according to the equations (1) through (7).

Corresponding units for obtaining and processing the measurement data can be provided for this purpose.

According to a further embodiment, a tabletop spirometer is provided, comprising the analysis unit. Providing an analysis unit in the body is then not absolutely necessary. A data communication between the sensor of the sensor unit and the sensors of the body having the analysis unit, however, is provided. This communication can take place by radio, infrared, or electrical current via cables or electromagnetic induction, and allows the analysis unit to access the measurement data of the sensors in order to analyze the same.

According to a further embodiment, a number of usage cycles of the sensor unit can be captured by the analysis unit. Here, the analysis unit can be provided in the body or in a tabletop spirometer, for example, and can count how often a sensor unit has been used. It can thus be determined whether a specified upper limit for the usage cycles of a sensor unit has been reached, using a comparison between the corresponding set value for the upper limit, and the counter reading according to the number of usages performed.

According to a further embodiment, the sensor unit comprises a storage unit for storing the captured, analyzed, or transmitted measurement data or the number of usage cycles of the spirometer. The counter readings determined by the analysis unit can thus be stored. Different measurement spirometers are preferably identified by a corresponding identification code, so that a new counter reading of the usage cycles can be associated with the new sensor unit when the sensor unit is replaced. Identification can take place on the basis of a data connection between the sensor unit and the body, that is, on the basis of an electrical contact via a cable or a contactless connection. Identification takes place automatically when the corresponding measurement spirometer is attached to the body, or due to an instruction by a user, such as by actuating a corresponding unit. If a previously used sensor unit is reattached to the body, then the analysis unit can identify this sensor unit, and can associate the unit with a previously determined cycle counter reading. It is thus ensured that, despite the interchangeability of the sensor unit, no sensor unit is used more often than has been determined using a corresponding preset reference value.

According to a further embodiment, a warning signal can be issued by the spirometer if a preset number of usage cycles of the sensor unit is reached. This alerts a user that an upper limit of usage cycles has been reached, and prompts the user to replace the sensor unit with a further sensor unit. It is also possible that when a preset number of usage cycles has been reached, the spirometer prevents usage until the sensor unit is replaced.

According to a method for operating a spirometer for measuring the pulmonary respiration of a test subject, having a sensor unit and a body, a sensor unit and a further sensor unit are calibrated for measuring a volume flow or a mass flow of air, so that substantially the same measurement values can be captured by both sensor units. The sensor unit is removably attached to the body. The sensor unit is then replaced by the calibrated further sensor unit if the sensor unit is no longer calibrated.

According to a further embodiment, a number of usage cycles of the sensor unit is captured by the analysis unit between the step of removably attaching and replacing. A warning signal is further issued upon reaching a preset number of usage cycles of the sensor unit of the spirometer.

The following detailed description of the invention is merely exemplary in nature and is not intended to limit the invention or the application and uses of the invention. Furthermore, there is no intention to be bound by any theory presented in the preceding background of the invention or the following detailed description of the invention.

DETAILED DESCRIPTION

Figure 1:
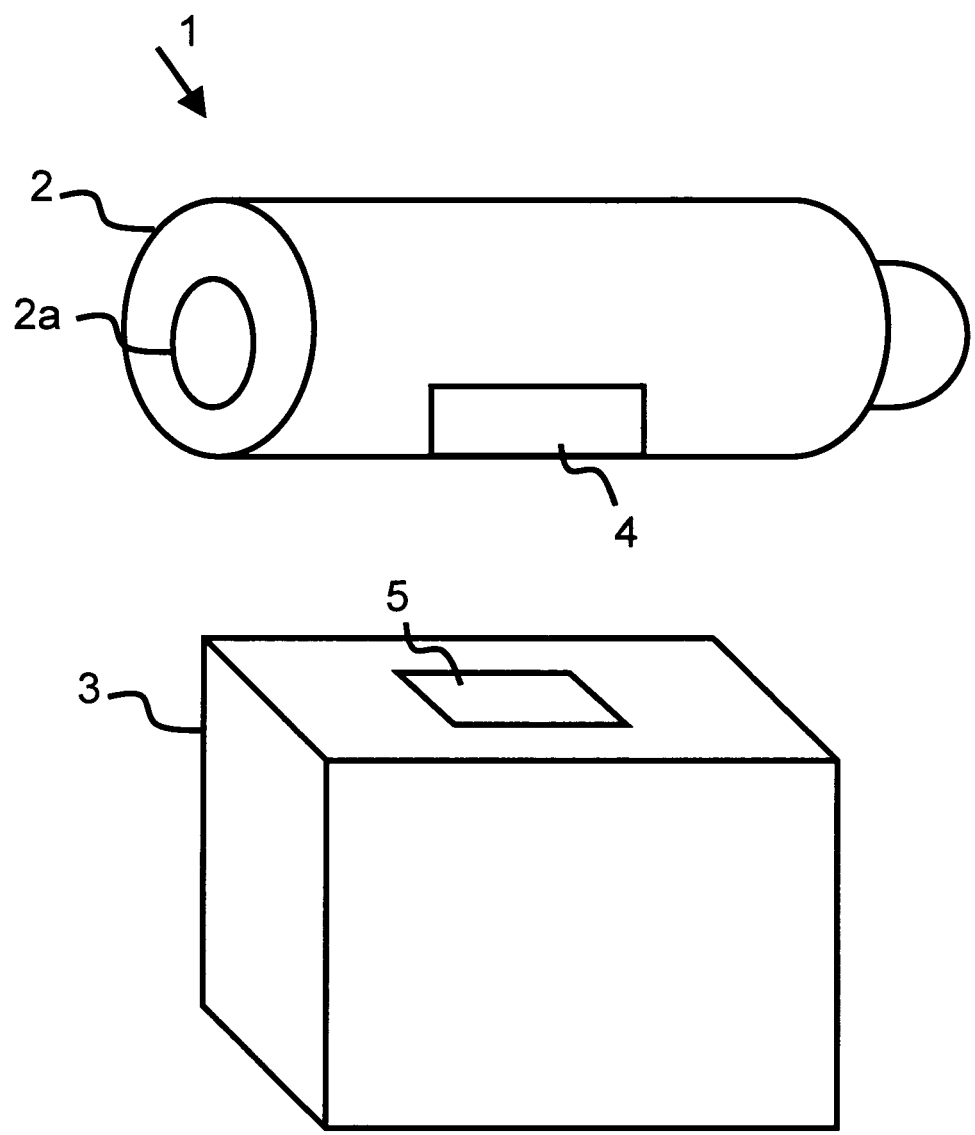
FIG. 1 shows a spirometer in sketched form according to a first embodiment.

FIG. 1 shows a sketch of a spirometer 1 for measuring pulmonary respiration of a test subject. Spirometer 1 comprises a sensor unit 2 having a flow tube 2a and a body 3. Sensor unit 2 can be removably attached to the body 3. An arrangement is shown, in which sensor unit 2 is not attached to body 3. Sensor unit 2 can be removably attached to body 3 by connecting members 4, 5. For this purpose, sensor unit 2 comprises a first connecting member 4, and body 5 comprises a second connecting member 5. Using connecting members 4, 5 it is possible to removably attach sensor unit 2 to body 4. At the same time a data connection between sensor unit 2 and body 3 may be established. To establish the data connection, connecting members 4 and 5 may comprise electrically conductive contacts.

Spirometer 1 is configured to measure the pulmonary respiration of the test subject. The test subject blows air into flow tube 2a during exhalation. The exhaled air flows through flow tube 2a of the sensor unit 2. Sensor unit 2 measures a mass flow of the air flowing through flow tube 2a. The test subject seals his mouth against flow tube 2a, so that all of the air that is inhaled or exhaled by the test subject flows through flow tube 2a. The mass flow of air flowing through flow tube 2a over time is measured by sensor unit 2, and used to characterize the pulmonary respiration of the test subject. Spirometer 1 may for example be used to determine the intensity of a lung contraction of the test subject, whereby illnesses can be diagnosed.

Sensor unit 2 can be removably attached to body 3 so that spirometer 1 serves for determining the lung function of a test subject. After use, sensor unit 2 can be removed from body 3, and replaced by a new, identical, sensor unit (not shown). The used sensor unit 2 can be disposed of, and a new sensor unit takes its place for the next test subject. The sensor unit 2 that was used on the body 3 by a first test subject for determining pulmonary respiration can hence be replaced as desired by a further sensor unit, particularly if a further test subject is to use the spirometer. Replacement of sensor unit 2 is also desirable, if sensor unit 2 is damaged, contaminated, or no longer sufficiently calibrated. Sensor units that can be attached to the body 3 are standardized to a set measurement standard in an unused state. That is, all sensor units are calibrated to a predetermined set of parameters and an expected use. The predetermined set of parameters may for example relate dimensions of the flow tube, such as its length and diameter. The expected use may for example relate to an expected lung volume or an expected breathing pressure of a test subject. The calibration of all sensor units 2 that can be attached to the body 3 ensures that a spirometer 1 having a still unused sensor unit 2 attached to the body 3 always provides reproducible measurement results.

Figure 2:
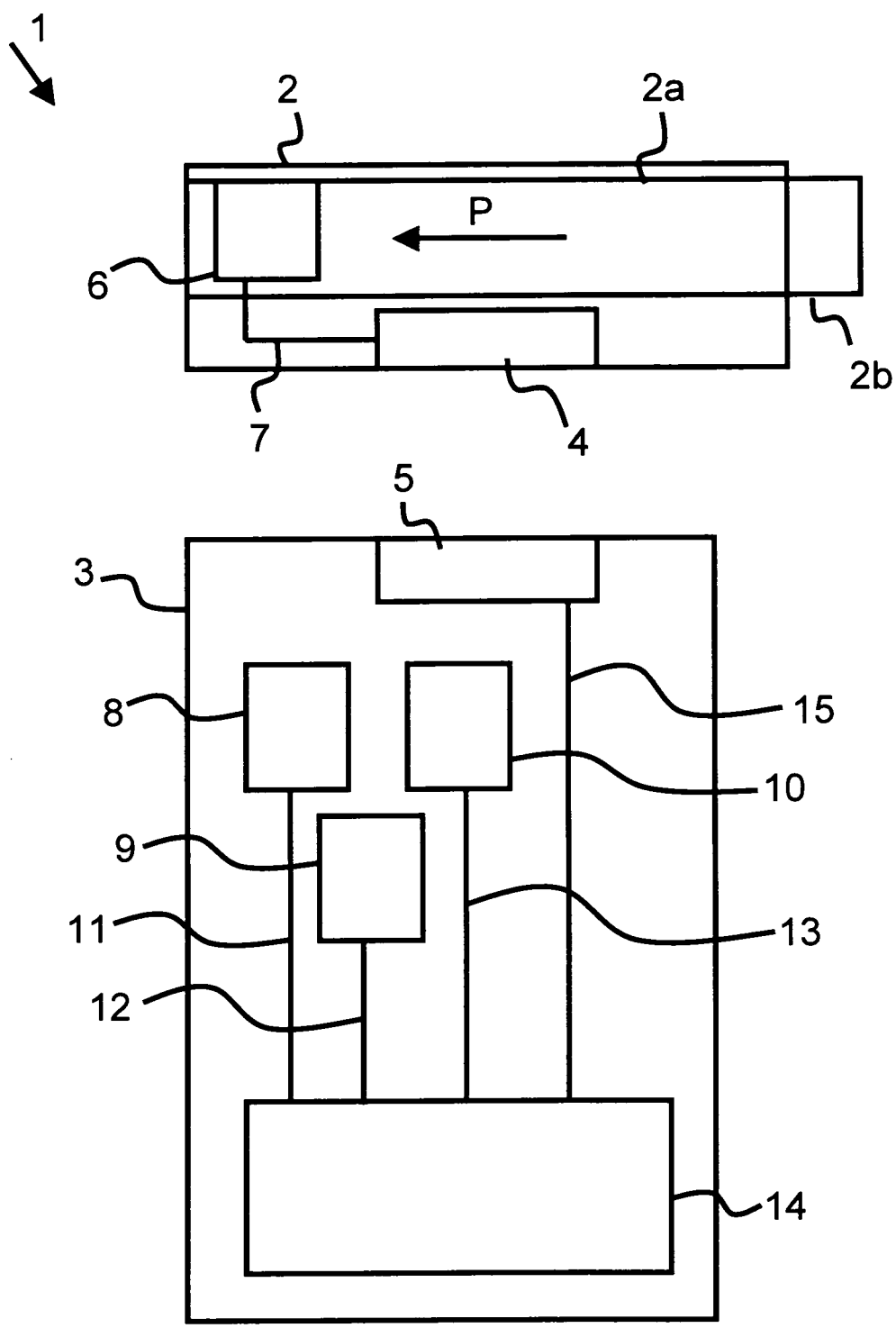
FIG. 2 shows a spirometer in sketched form according to the first embodiment.

FIG. 2 shows a further sketch of spirometer 1. Sensor unit 2 comprises flow tube 2a and can be attached to body 3. Sensor unit 2 comprises a mass flow sensor 6 provided for measuring the mass flow of air flowing through flow tube 2a of sensor unit 2. For this purpose, mass flow sensor 6 is disposed in flow tube 2a. The test subject can blow air into flow tube 2a, or draw air in through flow tube 2a. For this purpose, the flow tube 2a comprises a mouthpiece 2b, to which a test subject can apply his mouth. Mouthpiece 2b is configured such that the test subject can easily establish a sealed connection between his mouth and mouthpiece 2b, whereby all air that moves out of or into the test subject's lungs flows through flow tube 2a. The direction of the air flowing through flow tube 2a during an exhalation is indicated by arrow P. Consequently, during inhalation the air in flow tube 2a flows in the direction opposite the arrow P.

Mass flow sensor 6 is operatively connected to connecting member 4 through a data connection 7, so that an exchange of measurement data of mass flow sensor 6 through connecting member 4 can take place.

Body 3 comprises a temperature sensor 8, a humidity sensor 9, and a pressure sensor 10. Temperature sensor 8 is provided for measuring the temperature in the environment thereof. This temperature substantially corresponds to the temperature in the environment of the body 3 and the entire spirometer. Humidity sensor 9 is provided for measuring the humidity of the ambient air, and pressure sensor 10 is provided for measuring an air pressure in the environment thereof. An analysis unit 14 is provided and operatively connected to temperature sensor 8 by connection 11. Analysis unit 14 is also operatively connected to humidity sensor 9 by connection 12. Further, analysis unit 14 is operatively connected to pressure sensor 10 by connection 13. In result, data can be exchanged between analysis unit 14 and the three sensors 8, 9, and 10 of the body 3. Analysis unit 14 is also operatively connected to connecting member 5 of body 3 by connection 15. When sensor unit 2 is attached to body 3, a data connection is established through connecting members 4 and 5. This enables a data exchange between mass flow sensor 6, temperature sensor 8, humidity sensor 9, pressure sensor 10, and analysis unit 14. More specifically, analysis unit 14 can capture measurement data of all four sensors 6, 8, 9, and 10 of the spirometer 1, and determine characteristics of air flowing through sensor unit 2 responsive to receiving the measurement data. Such characteristics may be determined include mass flow, mass, volume flow, and volume of air flowing through sensor unit 2.

Data reflecting characteristics of the air flowing through flow tube 2a, e.g. the volume of air, can be communicated by the analysis unit 14 externally to a user of the spirometer 1. This communication may include a wired or wireless data communication, so that this information about the volume flow can be used for a diagnosis with respect to the lung function of a test subject. The measurement data of all sensors 6, 8, 9, and 10 of the spirometer 1 can thus not only be captured and analyzed, but also transmitted externally. Spirometer 1 may also comprise a display (not illustrated) for displaying the captured or analyzed measurement data. The analysis unit 14 can transmit the captured or analyzed data, for example to a loudspeaker, by means of which a warning signal can be issued if a preset number of usage cycles of the sensor unit 2 has been reached. For this purpose, the analysis unit 14 compares the captured number of usage cycles of each sensor unit 2 attached to the body 3 with a corresponding comparison value. If the captured number of usage cycles for a sensor unit 2 matches the corresponding preset number of usage cycles, then the analysis unit 14 can transmit corresponding information to a display unit or a loudspeaker, so that the corresponding warning message or a warning signal is issued. A user of spirometer 1 is then instructed to replace the sensor unit 2 with a new sensor unit.

In order to use the spirometer 1, a user attaches the sensor unit 2 to the body 3, whereby a data communication path is established between sensor unit 2 and body 3 via the connecting members 4, 5. A test subject places his mouth on the mouthpiece 2b of flow tube 2a of the sensor unit 2, and exhales through flow tube 2. All of the air of the exhalation thereby flows through the flow tube 2, and the mass flow sensor 6 disposed therein measures a total mass of the air flowing across the sensor, or a mass flow of the air over time. At nearly the same time, the temperature sensor 8, the humidity sensor 9, and the pressure sensor 10 measure the temperature, the humidity, and the air pressure in the environment of the spirometer 1. The analysis unit 14 receives the measurement values of all four sensors 6, 8, 9, 10 and determines from these values a volume flow of the air flowing or having flowed through the flow tube 2a. The analyzed results can then be transmitted by the analysis unit to a storage unit, a display unit, a loudspeaker, or further units, in order to store, display, or issue the results as a corresponding acoustic signal, or to allow further data processing steps.

If the sensor unit 2 is damaged, contaminated by pathogens, unsuitable for further use for hygienic reasons, or no longer allows reproducible measurements, then the sensor unit 2 can be removed from the body 3 by a user. Because the sensor unit 2 is removable and is constructed simply, it can simply be disposed of. A new, unused sensor unit is then attached to the body 3, so that a clean, calibrated spirometer 1 is provided for measuring the pulmonary respiration of a test subject.

While the present invention has been described with reference to exemplary embodiments, it will be readily apparent to those skilled in the art that the invention is not limited to the disclosed or illustrated embodiments but, on the contrary, is intended to cover numerous other modifications, substitutions, variations and broad equivalent arrangements that are included within the spirit and scope of the following claims.

What is claimed is:

1. A spirometer for measuring pulmonary respiration of a test subject, comprising:
a sensor unit, the sensor unit comprising
a flow tube,
a mass flow sensor disposed within the flow tube, the mass flow sensor being adapted to sense a mass flow of air flowing through the flow tube, and
a sensor identification code; and
a body, adapted to removably attach the sensor unit thereto, the body comprising a plurality of ambient air sensors adapted to sense a plurality of ambient air characteristics, the ambient air sensors being operatively connected to an analysis unit,
wherein the mass flow sensor becomes operatively connected to the analysis unit when the sensor unit is attached to the body, and
wherein the mass flow sensor comprises a first temperature element that is exposed to the mass flow of air flowing through the flow tube, and
wherein during operation of the spirometer the first temperature element is heated to a target temperature, and
wherein the mass flow of air flowing through the flow tube is derived from an amount of power that is required to maintain the target temperature of the first temperature element while being exposed to the mass flow of air flowing through the flow tube, and
wherein the sensor unit is identified by reading the sensor identification code through a data connection between the sensor unit and the body when the sensor unit is attached to the body, and
wherein the pulmonary respiration of the test subject is determined in the analysis unit by evaluating the mass flow of air flowing through the flow tube sensed by the mass flow sensor and the plurality of ambient air characteristics sensed by the plurality of ambient air sensors.

2. The spirometer as in claim 1,
wherein the plurality of ambient air sensors comprises a temperature sensor adapted to sense ambient air temperature, a humidity sensor adapted to sense ambient air humidity, and a pressure sensor adapted to sense ambient air pressure.

3. The spirometer as in claim 1, further comprising a second temperature element adapted to sense a temperature of air in the flow tube, wherein the target temperature of the first temperature element is a predetermined delta value above the temperature sensed by the second temperature element.

4. The spirometer as in claim 1, wherein the sensor unit is disposable and the body is reusable.

5. The spirometer as in claim 1, wherein the sensor unit is standardized with respect to a set measurement standard.

6. The spirometer as in claim 1, wherein the sensor unit is standardized with respect to a lung volume of the test subject or to a set mass flow.

7. The spirometer as in claim 2, wherein the pulmonary respiration of the test subject determined in the analysis unit is a volume flow of air flowing through the flow tube, or a volume of air flowing through the flow tube over time, or both as a function of the mass flow of air flowing through the flow tube, ambient air temperature, ambient air humidity, and ambient air pressure.

8. The spirometer as in claim 7, wherein the pulmonary respiration of the test subject determined in the analysis unit is communicated to a user of the spirometer.

9. The spirometer as in claim 1, wherein the analysis unit is located inside the body.

10. The spirometer as in claim 1, further comprising a tabletop housing which is operatively connected to the body, wherein the analysis unit is located inside the tabletop housing.

11. The spirometer as in claim 1, wherein a number of usage cycles of the sensor unit is associated with the sensor identification code and recorded by the analysis unit.

12. The spirometer as in claim 1, wherein the sensor unit further comprises a storage unit for storing data processed by the analysis unit, or a number of usage cycles of the sensor unit, or both.

13. The spirometer as in claim 12, wherein a warning signal is issued if a predetermined number of usage cycles of the sensor unit has been reached.

14. A method for operating the spirometer as in claim 1, comprising the steps of:
a) attaching the sensor unit to the body;
b) blowing air into the flow tube by the test subject;
c) repeating step b) as needed with the same test subject;
d) removing the sensor unit from the body; and
e) disposing the sensor unit.

15. The method as in claim 14, further comprising the step of
recording a number of usage cycles of the sensor unit in a storage unit within the sensor unit, the number of usage cycles being the number of times step b) is performed after step a) has been performed, and
issuing a warning, if a predetermined number of usage cycles has been reached.

* * * * *